United States Patent
Kumon et al.

(10) Patent No.: US 11,951,182 B2
(45) Date of Patent: Apr. 9, 2024

(54) COMBINATION THERAPY FOR TREATMENT OF THORACIC CANCER USING AD-REIC/DKK-3 AND A CHECKPOINT INHIBITOR

(71) Applicant: Momotaro-Gene Inc., Okayama (JP)

(72) Inventors: Hiromi Kumon, Okayama (JP); Bryan Burt, Houston, TX (US)

(73) Assignee: Momotaro-Gene Inc., Okayama (JP)

( * ) Notice: Subject to any disclaimer, the term of this patent is extended or adjusted under 35 U.S.C. 154(b) by 0 days.

(21) Appl. No.: 17/290,656

(22) PCT Filed: Nov. 1, 2019

(86) PCT No.: PCT/JP2019/043151
§ 371 (c)(1),
(2) Date: Apr. 30, 2021

(87) PCT Pub. No.: WO2020/091066
PCT Pub. Date: May 7, 2020

(65) Prior Publication Data
US 2021/0402010 A1 Dec. 30, 2021

Related U.S. Application Data

(60) Provisional application No. 62/831,108, filed on Apr. 8, 2019, provisional application No. 62/754,226, filed on Nov. 1, 2018.

(51) Int. Cl.
*A61K 48/00* (2006.01)
*A61K 38/17* (2006.01)
*A61K 39/00* (2006.01)
*A61K 39/395* (2006.01)
*A61P 35/00* (2006.01)
*C12N 15/86* (2006.01)

(52) U.S. Cl.
CPC ...... *A61K 48/0058* (2013.01); *A61K 38/1709* (2013.01); *A61K 39/3955* (2013.01); *A61K 48/0066* (2013.01); *A61P 35/00* (2018.01); *C12N 15/86* (2013.01); *A61K 2039/505* (2013.01); *C12N 2710/10043* (2013.01); *C12N 2710/10071* (2013.01)

(58) Field of Classification Search
None
See application file for complete search history.

(56) References Cited

U.S. PATENT DOCUMENTS

| | | | | |
|---|---|---|---|---|
| 8,658,611 B2* | 2/2014 | Kumon | ............... | C07K 14/4747 514/44 R |
| 8,658,612 B2* | 2/2014 | Kumon | ................. | C07K 14/47 514/44 R |
| 8,946,173 B2* | 2/2015 | Kumon | ................ | A61K 31/713 514/44 R |
| 9,222,107 B2* | 12/2015 | Kumon | ............... | A61K 38/1709 |
| 9,475,865 B2* | 10/2016 | Kumon | ................... | A61P 35/00 |
| 11,484,592 B2* | 11/2022 | Kumon | ................ | C12N 15/861 |
| 2010/0204308 A1 | 8/2010 | Namba et al. | | |
| 2011/0189237 A1 | 8/2011 | Kumon et al. | | |
| 2019/0015506 A1* | 1/2019 | Kumon | ................ | A61K 39/395 |

FOREIGN PATENT DOCUMENTS

| WO | WO-01/38528 A1 | 5/2001 | |
|---|---|---|---|
| WO | WO-2016170157 A1 * | 10/2016 | ......... A61K 31/5377 |
| WO | WO-2017/119499 A1 | 7/2017 | |

OTHER PUBLICATIONS

Tallón de Lara et al. (Swiss Medical Weekly Jun. 27, 2018, 148 (Suppl. 230): 17S) (Year: 2018).*
Shien et al. (Plos One Feb. 2014 9(2): e87900) (Year: 2014).*
International Search Report dated Jan. 28, 2020 in PCT/JP2019/043151.
Suzawa et al., "Distant Bystander Effect of RE1C/DKK3 Gene Therapy Through Immune System Stimulation in Thoracic Malignancies," Anticancer Research, 2017, 37:301-308.
U.S. National Institutes of Health, "MTG201 Plus Nivolumab in Patients with Relapsed Pleural Mesothelioma," last update Oct. 8, 2019, retrieved on Jan. 17, 2020 from https://clinicaltrials.gov/ct2/show/study/NCT04013334?term-REIC&draw-2&rank=4.
Watanabe et al., "A novel gene expression system strongly enhances the anticancer effects of a REIC/Dkk-3-encoding adenoviral vector," Oncology Reports, 2014, 31:1089-1095.

* cited by examiner

*Primary Examiner* — Peter J Reddig
(74) *Attorney, Agent, or Firm* — Foley & Lardner LLP

(57) ABSTRACT

An object of the present invention is to provide a method of treating thoracic cancer using a checkpoint inhibitor in combination with Ad-REIC/Dkk-3. The present invention is a pharmaceutical composition for treating thoracic cancer comprising REIC/Dkk-3 in combination with acheck point inhibitor and a method for treating thoracic cancer by administering Ad-REIC/Dkk-3 and a check point inhibitor to a thoracic cancer patient.

6 Claims, 15 Drawing Sheets

Specification includes a Sequence Listing.

Fig. 2 pshuttle- REIC-TSC

```
      (1)         (2)
XbaI-[REIC]-KpnI-[3xenh]-EcoRI
```

SEQ ID NO: 5

```
[T/CTAGA][GC acc][atg]cagcggcttggggccaccctgctgtgcctgctgctggcggcggcggt    (1)
ccccacggcccccgcgcccgctccgacggcgacctcggctccagtcaagcccggcccggctc
tcagctacccgcaggaggaggccaccctcaatgagatgttccgcgaggttgaggaactgatg
gaggacacgcagcacaaattgcgcagcgcggtggaagagatggaggcagaagaagctgctgc
taaagcatcatcagaagtgaacctggcaaacttacctcccagctatcacaatgagaccaaca
cagacacgaaggttggaaataataccatccatgtgcaccgagaaattcacaagataaccaac
aaccagactggacaaatggtcttttcagagacagttatcacatctgtgggagacgaagaagg
cagaaggagccacgagtgcatcatcgacgaggactgtgggcccagcatgtactgccagtttg
ccagcttccagtacacctgccagccatgccggggccagaggatgctctgcacccgggacagt
gagtgctgtggagaccagctgtgtgtctgggtcactgcaccaaaatggccaccaggggcag
caatgggaccatctgtgacaaccagagggactgccagccggggctgtgctgtgccttccaga
gaggcctgctgttccctgtgtgcacaccccctgcccgtggagggcgagctttgccatgacccc
gccagccggcttctggacctcatcacctgggagctagagcctgatggagccttggaccgatg
cccttgtgccagtggcctcctctgccagccccacagccacagcctggtgtatgtgtgcaagc
cgaccttcgtggggagccgtgaccaagatggggagatcctgctgcccagagaggtccccgat
gagtatgaagttggcagcttcatggaggaggtgcgccaggagctggaggacctggagaggag
cctgactgaagagatggcgctgggggagcctgcggctgccgccgctgcactgctgggagggg
aagagatt[tagGG][GGTAC/C][CCG]GCtagatgactaacGTTTAAACCCGCTGATCAGCCTCGA
CTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATTGGGAAG
ACAATAGCAGGCATGCTGGGGATGCGGTGGGCTCTATGG[cggagtactgtcctccg]cttccc    (2)
acgtggcggagggactggggacccgggcacccgtcctgccccttcaccttccagctccgcct
cctccgcgcggaccccgccccgtcccgacccctcccgggtccccggccccagcccctccggg
ccctcccagcccctccccttccttccgcggccccgccctctcctcgcggcgcgagttttTGG
AAAGTCCCCAGGCTCCCCAGCAGGCAGAAGTATCCAAAGCATCCATCTCAATTAGTCAGCAA
CCAGGTGTGGAAAGTCCCCAGGCTCCCCAGCAGGCAGAAGTATCCAAAGCATCCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTGG[AGGCCA]AGGCTTTTGCAAA
AAGCTCcgttacataacttacggtaaatggcccgcctggctgaccgcccaacgacccccgcc
cattgacgtcaataatgacgtatgttcccatagtaacgccaataggggactttccattgacgt
caatgggtggagtatttacggtaaactgcccacttggcagtacatcaagtgtatcatatgcc
aagtacgccccctattgacgtcaatgacggtaaatggcccgcctggcattatgcccagtaca
tgaccttatgggactttcctacttggcagtacatctacgtattagtcatcgctattaccatg
gtgatgcggttttggcagtacatcaatgggcgtggatagcggtttgactcacggggatttcc
aagtctccaccccattgacgtcaatgggagtttgttttggcaccaaaatcaacgggactttc
caaaatgtcgtaacaactccgccccattgacgcaaatgggcggtaggcgtg[TTGCCG][G/AAT]
[TC]
```

Fig. 3

Tumor burden study of MTG-201

| Group | Drug | N (25) | D0 9/19 | D10 9/29 | D14 10/3 | D16 10/5 | D21 10/10 | D28 10/17 |
|---|---|---|---|---|---|---|---|---|
| 1 | Ad-LacZ | 5 | Cancer Cell Injection (5x10⁵/100µl, SC with Matrigel) | Transfer | Ad-LacZ 5x10¹⁰ virus particle/100µl | Ad-LacZ 5x10¹⁰ virus particle/100µl | | Sacrifice |
| 2 | Ad-LacZ Anti-PD1 antibody | 5 | | | Ad-LacZ 5x10¹⁰ virus particle/50µl | Ad-LacZ 5x10¹⁰ virus particle/100µl | Anti-PD1 antibody 250µg/100µl | |
| | | | | | Anti-PD1 antibody 250µg/50µl | | | |
| 3 | MTG-201 | 5 | | | MTG-201 5x10¹⁰ virus particle/100µl | MTG-201 5x10¹⁰ virus particle/100µl | | |
| 4 | MTG-201 Anti-PD1 antibody | 5 | | | MTG-201 5x10¹⁰ virus particle/50µl | MTG-201 5x10¹⁰ virus particle/100µl | Anti-PD1 antibody 250µg/100µl | |
| | | | | | Anti-PD1 antibody 250µg/50µl | | | |
| 5 | Anti-PD1 antibody | 5 | | | Anti-PD1 antibody 250µg/100µl | | Anti-PD1 antibody 250µg/100µl | |
| Total injection volume | | | 100µl (SC) | | 100µl (SC: intratumoral) | 100µl (SC) | 100µl (SC) | |

SEQUENCE LISTING

```
<160> NUMBER OF SEQ ID NOS: 6

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1 atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
  1               5                  10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
             20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
         35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
     50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
 65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
```

|     |     |     |     |     |     |     | 85  |     |     |     |     | 90  |     |     |     |     | 95  |     |      |
| --- | --- | --- | --- | --- | --- | --- | --- | --- | --- | --- | --- | --- | --- | --- | --- | --- | --- | --- | ---- |
| gag | acc | aac | aca | gac | acg | aag | gtt | gga | aat | aat | acc | atc | cat | gtg | cac |     |     |     | 336  |
| Glu | Thr | Asn | Thr | Asp | Thr | Lys | Val | Gly | Asn | Asn | Thr | Ile | His | Val | His |     |     |     |      |
|     |     |     | 100 |     |     |     |     | 105 |     |     |     |     | 110 |     |     |     |     |     |      |

```
cga gaa att cac aag ata acc aac cag gct cga caa atg gtc ttt           384
Arg Glu Ile His Lys Ile Thr Asn Asn Gln Ala Arg Gln Met Val Phe
            115                 120                 125 tca gag aca gtt atc aca tct gtg gga gac gaa gaa ggc aga agg agc       432
Ser Glu Thr Val Ile Thr Ser Val Gly Asp Glu Glu Gly Arg Arg Ser
130                 135                 140 cac gag tgc atc atc gac gag gac tgt ggg ccc agc atg tac tgc cag       480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg       528
Phe Ala Ser Phe Gln Tyr Thr Cys Gln Pro Cys Arg Gly Gln Arg Met
            165                 170                 175 ctc tgc acc cgg gac agt gag tgc tgt gga gac cag ctg tgt gtc tgg       576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt       624
Gly His Cys Thr Lys Met Ala Thr Arg Gly Ser Asn Gly Thr Ile Cys
            195                 200                 205 gac aac cag agg gac tgc cag ccg ggg ctg tgc tgt gcc ttc cag aga       672
Asp Asn Gln Arg Asp Cys Gln Pro Gly Leu Cys Cys Ala Phe Gln Arg
210                 215                 220 ggc ctg ctg ttc cct gtg tgc ata ccc ctg ccc gtg gag ggc gag ctt       720
Gly Leu Leu Phe Pro Val Cys Ile Pro Leu Pro Val Glu Gly Glu Leu
225                 230                 235                 240 tgc cat gac ccc gcc agc cgg ctt ctg gac ctc atc acc tgg gag cta       768
Cys His Asp Pro Ala Ser Arg Leu Leu Asp Leu Ile Thr Trp Glu Leu
            245                 250                 255 gag cct gat gga gcc ttg gac cga tgc cct tgt gcc agt ggc ctc ctc       816
Glu Pro Asp Gly Ala Leu Asp Arg Cys Pro Cys Ala Ser Gly Leu Leu
            260                 265                 270 tgc cag ccc cac agc cac agc ctg gtg tat gtg tgc aag ccg acc ttc       864
Cys Gln Pro His Ser His Ser Leu Val Tyr Val Cys Lys Pro Thr Phe
            275                 280                 285 gtg ggg agc cgt gac caa gat ggg gag atc ctg ctg ccc aga gag gtc       912
Val Gly Ser Arg Asp Gln Asp Gly Glu Ile Leu Leu Pro Arg Glu Val
            290                 295                 300 ccc gat gag tat gaa gtt ggc agc ttc atg gag gag gtg cgc cag gag       960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag      1008
Leu Glu Asp Leu Glu Arg Ser Leu Thr Glu Glu Met Ala Leu Gly Glu
            325                 330                 335 cct gcg gct gcc gcc gct gca ctg ctg gga ggg gaa gag att tag          1053
Pro Ala Ala Ala Ala Ala Leu Leu Gly Gly Glu Glu Ile
            340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30
```

Lys Pro Gly Pro Ala Leu Ser Tyr Pro Gln Glu Ala Thr Leu Asn
            35                  40                  45

Glu Met Phe Arg Glu Val Glu Leu Val Glu Asp Thr Gln His Lys
     50                  55                  60

Leu Arg Ser Ala Val Glu Glu Met Glu Ala Glu Ala Ala Ala Lys
 65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
            115                 120                 125

Ser Glu Thr Val Ile Thr Ser Val Gly Asp Glu Glu Gly Arg Arg Ser
        130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
            340                 345                 350

<210> SEQ ID NO 3
<211> LENGTH: 117
<212> TYPE: DNA
<213> ORGANISM: Homo sapiens

<400> SEQUENCE: 3
atgcagcggc ttggggccac cctgctgtgc ctgctactgg cggcggcggt ccccacggcc    60
cccgcgcccg ctccgacggc gacctcggct ccagtcaagc ccggccggc tctcagc    117

<210> SEQ ID NO 4
<211> LENGTH: 234
<212> TYPE: DNA
<213> ORGANISM: Homo sapiens

<400> SEQUENCE: 4

```
atgcagcggc ttggggccac cctgctgtgc ctgctactgg cggcggcggt ccccacggcc      60
cccgcgcccg ctccgacggc gacctcggct ccagtcaagc ccggcccggc tctcagctac     120
ccgcaggagg aggccaccct caatgagatg ttccgcgagg ttgaggaact ggtgggaggac    180
acgcagcaca aattgcgcag cgcggtggaa gagatggagg cagaagaagc tgct           234
```

<210> SEQ ID NO 5
<211> LENGTH: 2355
<212> TYPE: DNA
<213> ORGANISM: Artificial
<220> FEATURE:
<223> OTHER INFORMATION: Synthetic

<400> SEQUENCE: 5

```
tctagagcac catgcagcgg cttggggcca ccctgctgtg cctgctgctg gcggcggcgg      60
tccccacggc cccgcgcccc gctccgacgg cgacctcggc tccagtcaag cccggcccgg     120
ctctcagcta cccgcaggag gaggccaccc tcaatgagat gttccgcgag gttgaggaac     180
tgatggagga cacgcagcac aaattgcgca gcgcggtgga agagatggag gcagaagaag     240
ctgctgctaa agcatcatca gaagtgaacc tggcaaactt acctcccagc tatcacaatg     300
agaccaacac agacacgaag gttggaaata ataccatcca tgtgcaccga gaaattcaca     360
agataaccaa caaccagact ggacaaatgg tcttttcaga cacagttatc acatctgtgg     420
gagacgaaga aggcagaagg agccacgagt gcatcatcga cgaggactgt gggcccagca     480
tgtactgcca gtttgccagc ttccagtaca cctgccagcc atgccggggc cagaggatgc     540
tctgcacccg ggacagtgag tgctgtggag accagctgtg tgtctggggt cactgcacca     600
aaatggccac caggggcagc aatgggacca tctgtgacaa ccagagggac tgccagccgg     660
ggctgtgctg tgccttccag agaggcctgc tgttccctgt gtgcacaccc ctgcccgtgg     720
agggcgagct ttgccatgac cccgccagcc ggcttctgga cctcatcacc tgggagctag     780
agcctgatgg agccttggac cgatgccctt gtgccagtgg cctcctctgc agccccaca     840
gccacagcct ggtgtatgtg tgcaagccga ccttcgtggg gagccgtgac caagatgggg     900
agatcctgct gcccagagag gtccccgatg agtatgaagt tggcagcttc atggaggagg     960
tgcgccagga gctggaggac ctggagagga gcctgactga agagatggcg ctggggagc    1020
ctgcggctgc cgccgctgca ctgctgggag gggaagagat ttagggggta ccccggctag    1080
atgactaacg tttaaacccg ctgatcagcc tcgactgtgc cttctagttg ccagccatct    1140
gttgttgtgcc cctccccgt gccttccttg accctggaag gtgccactcc cactgtcctt    1200
tcctaataaa atgaggaaat tgcatcgcat tgtctgagta ggtgtcattc tattctgggg    1260
ggtgggggtgg ggcaggacag caaggggag gattgggaag acaatagcag gcatgctggg    1320
gatgcggtgg gctctatggc ggagtactgt cctccgcttc ccacgtggcg gagggactgg    1380
ggacccgggc accgtcctg cccttcacc ttcagctcc gcctcctccg cgcggacccc       1440
gccccgtccc gaccctccc gggtccccgg ccagccccc tccgggccct cccagccct       1500
cccttcctt tccgcggccc cgccctctcc tcgcggcgcg agttttggaa agtcccagg      1560
ctccccagca ggcagaagta ccaaagcat ccatctcaat tagtcagcaa ccaggtgtgg    1620
aaagtcccca ggctcccag caggcagaag tatccaaagc atccatctca attagtcagc    1680
aaccatagtc ccgcccctaa ctccgcccat ccgcccccta actccgccca gttccgccca    1740
ttctccgccc catggctgac taatttttt tatttatgca gaggccgagg ccgcctctgc    1800
```

-continued

```
ctctgagcta ttccagaagt agtgaggagg ctttttttgga ggccaaggct tttgcaaaaa      1860
gctccgttac ataacttacg gtaaatggcc cgcctggctg accgcccaac gaccccgcc       1920
cattgacgtc aataatgacg tatgttccca tagtaacgcc aatagggact ttccattgac      1980
gtcaatgggt ggagtattta cggtaaactg cccacttggc agtacatcaa gtgtatcata      2040
tgccaagtac gccccctatt gacgtcaatg acggtaaatg gcccgcctgg cattatgccc      2100
agtacatgac cttatgggac tttcctactt ggcagtacat ctacgtatta gtcatcgcta      2160
ttaccatggt gatgcggttt tggcagtaca tcaatgggcg tggatagcgg tttgactcac      2220
ggggatttcc aagtctccac cccattgacg tcaatgggag tttgttttgg caccaaaatc      2280
aacgggactt tccaaaatgt cgtaacaact ccgccccatt gacgcaaatg ggcggtaggc      2340
gtgttgccgg aattc                                                      2355
```

<210> SEQ ID NO 6
<211> LENGTH: 1285
<212> TYPE: DNA
<213> ORGANISM: Artificial
<220> FEATURE:
<223> OTHER INFORMATION: Synthetic

<400> SEQUENCE: 6

```
gtttaaaccc gctgatcagc ctcgactgtg ccttctagtt gccagccatc tgttgtttgc        60
ccctcccccg tgccttcctt gaccctggaa ggtgccactc ccactgtcct ttcctaataa       120
aatgaggaaa ttgcatcgca ttgtctgagt aggtgtcatt ctattctggg gggtggggtg       180
gggcaggaca gcaaggggga ggattgggaa gacaatagca ggcatgctgg ggatgcggtg       240
ggctctatgg cggagtactg tcctccgctt cccacgtggc ggagggactg gtcctccgct       300
tcccacgtgg cggagggact ggggacccgg gcacccgtcc tgccccttca ccttccagct       360
ccgcctcctc cgcgcggacc ccgccccgtc ccgaccccttc ccgggtcccc ggcccagccc      420
cctccgggcc ctcccagccc ctccccttcc tttccgcggc ccgccctct cctcgcggcg       480
cgagttttgg aaagtcccca ggctccccag caggcagaag tatccaaagc atccatctca      540
attagtcagc aaccaggtgt ggaaagtccc caggctcccc agcaggcaga agtatccaaa      600
gcatccatct caattagtca gcaaccatag tccgcccct aactccgccc atcccgcccc       660
taactccgcc cagttccgcc cattctccgc cccatggctg actaattttt tttatttatg      720
cagaggccga ggccgcctct gcctctgagc tattccagaa gtagtgagga ggcttttttg      780
gaggccaagg cttttgcaaa aagctccgtt acataactta cggtaaatgg cccgcctggc      840
tgaccgccca acgaccccg cccattgacg tcaataatga cgtatgttcc catagtaacg       900
ccaatagggga ctttccattg acgtcaatgg gtggagtatt tacggtaaac tgcccacttg      960
gcagtacatc aagtgtatca tatgccaagt acgccccta ttgacgtcaa tgacggtaaa      1020
tggcccgcct ggcattatgc ccagtacatg accttatggg actttcctac ttggcagtac      1080
atctacgtat tagtcatcgc tattaccatg gtgatgcggt tttggcagta catcaatggg      1140
cgtggatagc ggtttgactc acggggattt ccaagtctcc accccattga cgtcaatggg      1200
agtttgttttt ggcaccaaaa tcaacgggac tttccaaaat gtcgtaacaa ctccgcccca      1260
ttgacgcaaa tgggcggtag gcgtg                                           1285
```

COMBINATION THERAPY FOR TREATMENT OF THORACIC CANCER USING AD-REIC/DKK-3 AND A CHECKPOINT INHIBITOR

CROSS-REFERENCE TO RELATED APPLICATIONS

This application is the U.S. National Stage of PCT/JP2019/043151, filed Nov. 1, 2019, which claims priority to U.S. Provisional Applications 62/754,226, filed Nov. 1, 2018 and 62/831,108, filed Apr. 8, 2019.

The instant application contains a Sequence Listing which has been submitted in ASCII format via EFS-WEB and is hereby incorporated by reference in its entirety. Said ASCII copy, created on Apr. 29, 2021, is named sequence.txt and is 13,702 bytes.

TECHNICAL FIELD

The present invention relates to a combination therapy for treatment of thoracic cancer using Ad-REIC/Dkk-3 and a checkpoint inhibitor.

BACKGROUND ART

REIC/Dkk-3 gene is known to be a gene relating to cell immortalization. It has been reported that the expression of this gene is suppressed in cancer cells. It has also been reported that the REIC/Dkk-3 gene has been used for cancer therapy (Patent Document 1).

A check point inhibitor such as anti-PD-1 (Programmed cell death 1) antibody, anti-PD-L1 (Programmed cell-death ligand 1), and the like are known to be useful for various malignant tumors.

CITATION LIST

Patent Literature

PTL 1: International Patent Publication WO01/038528

SUMMARY OF INVENTION

Technical Problem

An object of the present invention is to provide a method of treating thoracic cancer using a checkpoint inhibitor in combination with Ad-REIC/Dkk-3.

Solution to Problem

The present inventors have examined the effect of the combination use of REIC/Dkk-3 and a checkpoint inhibitor for the treatment of thoracic cancers.

The present inventors found that the combination use of REIC/Dkk-3 and a checkpoint inhibitor enhances a systemic T cell response and anti-tumor responses. It indicates that the combination use of REIC/Dkk-3 and a checkpoint inhibitor is useful method for treating thoracic cancer.

Specifically, the present invention is as follows.

[1] A pharmaceutical composition for treating thoracic cancer comprising an Ad-REIC/Dkk-3 in combination with a check point inhibitor, wherein the Ad-REIC/Dkk-3 is an adenovirus vector having a DNA construct which is prepared by ligating, from the 5' terminal side:
(i) a CMV promoter;
(ii) the following REIC/Dkk-3 DNA:
(a) DNA comprising the nucleotide sequence shown in SEQ ID NO: 1,
(b) DNA having at least 90% sequence identity with the nucleotide sequence shown in SEQ ID NO:1,
(iii) a polyA addition sequence; and
(iv) enhancers prepared by linking an hTERT (Telomerase Reverse Transcriptase) enhancer, an SV40 enhancer, and a CMV enhancer in this order.

[2] The pharmaceutical composition of [1], wherein the check point inhibitor is an anti-PD-1 antibody or anti-PD-L1 antibody.

[3] The pharmaceutical composition of [1], wherein the thoracic cancer is a mesothelioma.

[4] A method for treating cancer by administering an Ad-REIC/Dkk-3 and a check point inhibitor to a thoracic cancer patient, wherein the Ad-REIC/Dkk-3 is an adenovirus vector having a DNA construct which is prepared by ligating, from the 5' terminal side:
(i) a CMV promoter;
(ii) the following REIC/Dkk-3 DNA:
(a) DNA comprising the nucleotide sequence shown in SEQ ID NO: 1,
(b) DNA having at least 90% sequence identity with the nucleotide sequence shown in SEQ ID NO:1,
(iii) a polyA addition sequence; and
(iv) enhancers prepared by linking an hTERT (Telomerase Reverse Transcriptase) enhancer, an SV40 enhancer, and a CMV enhancer in this order.

[5] The method for treating cancer of [4], wherein the check point inhibitor is an anti-PD-1 antibody or anti-PD-L1 antibody.

[6] The method for treating cancer of [4], wherein the thoracic cancer is a mesothelioma.

[7] A method for combining an Ad-REIC/Dkk-3 with a check point inhibitor to treat thoracic cancer.

[8] The method according to [7], wherein the check point inhibitor is an anti-PD-1 antibody or an anti-PD-L1 antibody.

[9] The method according to [7], wherein the check point inhibitor is an anti-PD-1 antibody.

[10] The method according to [7], wherein the check point inhibitor is an anti-PD-L1 antibody.

[11] Use of anti-PD-1 and anti-PD-L1 antibodies to manipulate the immune system such that thoracic cancer expresses PD-1 and PD-L1 on the cell surface making it susceptible to REIC/Dkk-3 gene (REIC/Dkk-3-induced anti-tumor immunity; CTLs induced by REIC/Dkk-3).

[12] A method for combining an Ad-REIC/Dkk-3 with a check point inhibitor in the manufacture of a medicine to treat thoracic cancer, wherein the Ad-REIC/Dkk-3 is an adenovirus vector having a DNA construct which is prepared by ligating, from the 5' terminal side:
(i) a CMV promoter;
(ii) the following REIC/Dkk-3 DNA:
(a) DNA comprising the nucleotide sequence shown in SEQ ID NO: 1,
(b) DNA having at least 90% sequence identity with the nucleotide sequence shown in SEQ ID NO:1,
(iii) a polyA addition sequence; and
(iv) enhancers prepared by linking an hTERT (Telomerase Reverse Transcriptase) enhancer, an SV40 enhancer, and a CMV enhancer in this order.

[13] The method according to [12], wherein the check point inhibitor is an anti-PD-1 antibody or an anti-PD-L1 antibody.

[14] A drug for treating thoracic cancer, which comprises REIC/Dkk-3 as an active in-gredient and used in combination with a check point inhibitor, wherein the Ad-REIC/Dkk-3 is an adenovirus vector having a DNA construct which is prepared by ligating, from the 5' terminal side:
(i) a CMV promoter;
(ii) the following REIC/Dkk-3 DNA:
(a) DNA comprising the nucleotide sequence shown in SEQ ID NO: 1,
(b) DNA having at least 90% sequence identity with the nucleotide sequence shown in SEQ ID NO:1,
(iii) a polyA addition sequence; and
(iv) enhancers prepared by linking an hTERT (Telomerase Reverse Transcriptase) enhancer, an SV40 enhancer, and a CMV enhancer in this order.

[15] The drug of [14], wherein the check point inhibitor is an anti-PD-1 antibody or anti-PD-L1 antibody.

[16] The drug of [14], wherein the thoracic cancer is a mesothelioma.

Advantageous Effects of Invention

Ad-REIC/Dkk-3 and the checkpoint inhibitor have synergy effect in treating thoracic cancers.

BRIEF DESCRIPTION OF DRAWINGS

FIG. 2 shows the sequence of Ad-REIC/Dkk-3.
FIG. 3 shows the study schema for MTG-201 tumor burden study (SC injection model).

The present specification incorporates the contents described in the specification and drawings of U.S. Provisional Applications No. 62/754,226 and No. 62/831,108 based on which the priority of the present application is claimed.

DESCRIPTION OF EMBODIMENTS

The combination therapy of the present invention uses a checkpoint inhibitor in combination with Ad-REIC/Dkk-3.

A checkpoint inhibitor includes anti-PD-1 (Programmed cell death 1) antibody, anti-PD-L1 (Programmed cell-death ligand 1), and the like.

The nucleotide sequence of REIC/Dkk-3 gene DNA is shown in SEQ ID NO: 1 of the sequence listing. Furthermore, the amino acid sequence of the REIC that is encoded by REIC/Dkk-3 DNA is shown in SEQ ID NO: 2 of the sequence listing. DNA having at least 85%, preferably at least 90%, further preferably at least 95%, and particularly preferably at least 97% sequence identity with the nucleotide sequence shown in SEQ ID NO: 1, when calculated using BLAST (Basic Local Alignment Search Tool) at the National Center for Biological Information (NCBI) or the like (with the use of, for example, default (i.e., initial) parameters) is included in REIC/Dkk-3 DNA.

A fragmental nucleotide of REIC/Dkk-3 can also be used. Examples of such a nucleotide comprising a nucleotide sequence ranging from the $1^{st}$ nucleotide to any single nucleotide from the $117^{th}$ to the $234^{th}$ nucleotides in the nucleotide sequence of REIC/Dkk-3 DNA shown in SEQ ID NO: 1 include the polynucleotide (SEQ ID NO: 3) ranging from the $1^{st}$ to the $117^{th}$ nucleotides and the polynucleotide (SEQ ID NO: 4) ranging from the $1^{st}$ the 234th nucleotides.

The REIC/Dkk-3 gene can be introduced into a subject in accordance with a con-ventional technique.

Examples of techniques for constructing an expression cassette can be obtained by inserting REIC/Dkk-3 DNA into a pShuttle vector (Clonetech) containing a foreign gene insertion site downstream of a commercial CMV promoter, and a BGA polyA sequence downstream of the insertion site, and then ligating an hTERT (Telomerase Reverse Transcriptase) enhancer, an SV40 enhancer, and a CMV enhancer in this order to a site downstream of the BGA polyA sequence.

The DNA construct can be prepared according to the descriptions of WO2011/062298, U52012-0309050, WO2012/161352 and U52014-0147917, which are incorporated herein by reference in their entirety.

Figure 1:
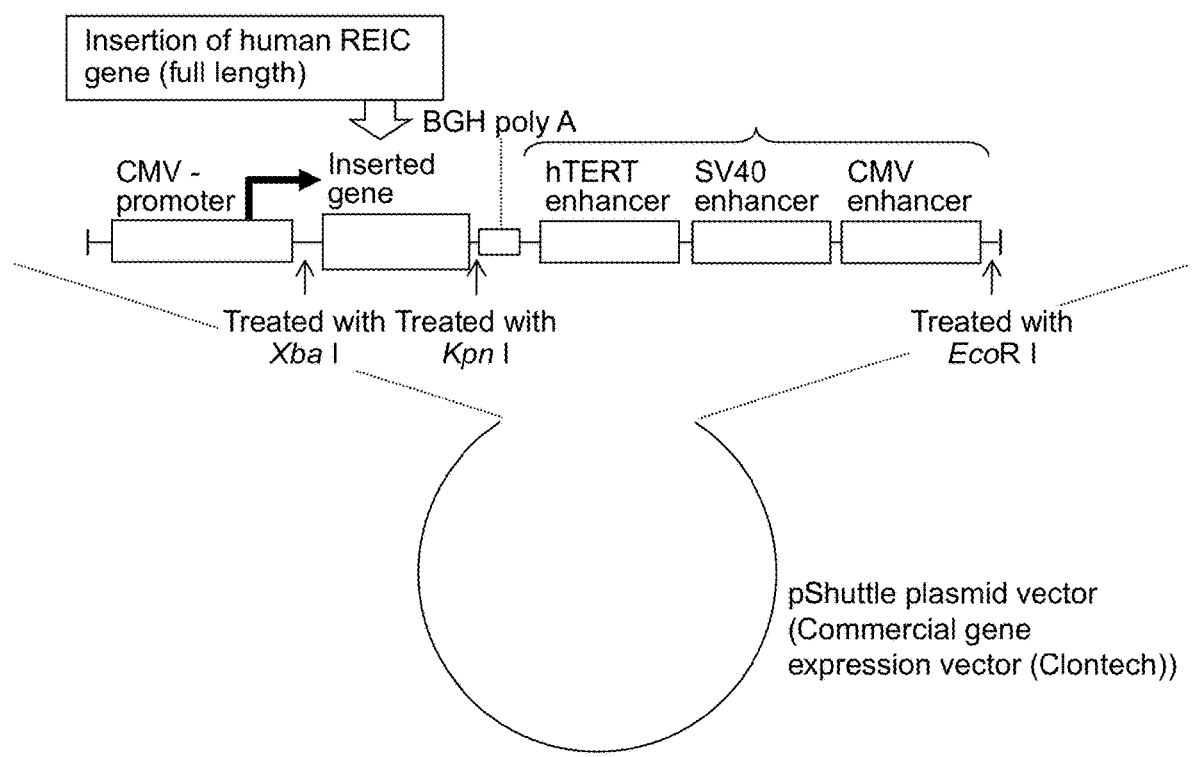
FIG. 1 shows an example of the structure of Ad-REIC/Dkk-3.

According to the present invention, an adenovirus vector comprising REIC/Dkk-3 DNA is called "Ad-REIC" or "Ad-REIC/Dkk-3." A vector system containing the DNA construct above is referred as an SGE (Super Gene Expression) system. For example, an adenovirus vector containing a DNA construct that contains REIC/Dkk-3 DNA is referred to such as "Ad5-SGE-REIC/Dkk-3." FIG. 1 shows an example of the structure of Ad-REIC/Dkk-3 and FIG. 2 shows the sequence of Ad-REIC/Dkk-3.

The DNA construct comprised in the Ad-REIC/Dkk-3 is prepared by ligating a CMV (cytomegarovirus) promoter to a site upstream of REIC/Dkk-3 DNA, and a polyA addition sequence (polyadenylation sequence, polyA) to a site downstream of REIC/Dkk-3 DNA. Moreover, enhancers (3×enh) prepared by linking an hTERT (Telomerase Reverse Transcriptase) enhancer, an SV40 enhancer, and a CMV (cytomegarovirus) enhancer in this order are ligated to a site downstream of the polyA addition sequence. Specifically, the DNA construct is prepared by ligating, from the 5' terminal side, (i) a CMV promoter, (ii) REIC/Dkk-3 DNA, (iii) a polyA addition sequence, and (iv) enhancers prepared by linking the hTER (Telomerase Reverse Transcriptase) enhancer, the SV40 enhancer, and the CMV enhancer in this order.

The structure of a portion of the DNA construct containing REIC/Dkk-3 DNA of the present invention, which lacks the CMV promoter, is shown in FIG. 2, and the sequence thereof is shown in SEQ ID NO: 5. In FIG. 2, a BGA polyA sequence is contained between REIC/Dkk-3 DNA and 3×enh. The DNA construct containing REIC/Dkk-3 DNA of the present invention has a CMV promoter upstream (5' side) of the sequence shown in SEQ ID NO: 5. SEQ ID NO: 6 shows the nucleotide sequence of the region containing BGH poly A and three enhancers (contained in the above construct). In FIG. 2, portions (1) and (2) enclosed by frames in the nucleotide sequence indicate DNA encoding the REIC/Dkk-3 protein and the three enhancers (3×enh), respectively.

The above elements should be functionally linked (ligated) to each other. The expression used herein, "functionally linked (ligated) to each other" means that elements are linked or ligated to each other so that each element can exhibit its functions so as to enhance the expression of a gene to be expressed.

That is to say, the DNA construct of "Ad-REIC/Dkk-3" is:
[1] A DNA construct for the expression of REIC/Dkk-3 DNA, which is prepared by ligating, from the 5' terminal side:
  (i) a CMV promoter;
  (ii) the following REIC/Dkk-3 DNA:
  (a) DNA comprising the nucleotide sequence shown in SEQ ID NO: 1,
  (b) DNA having at least 90%, 95%, 97% or 98% sequence identity with the nucleotide sequence shown in SEQ ID NO:1,
  (iii) a polyA addition sequence; and
  (iv) enhancers prepared by linking an hTERT (Telomerase Reverse Transcriptase) enhancer, an SV40 enhancer, and a CMV enhancer in this order;
[2] The DNA construct according to [1] above, wherein the polyA addition sequence is a polyA addition sequence (BGA polyA) derived from a bovine growth hormone gene; and
[3] The DNA construct according to [1] or [2] above, containing the nucleotide sequence shown in SEQ ID NO: 5, wherein (ii) REIC/Dkk-3 DNA, (iii) the polyA addition sequence, and (iv) enhancers prepared by linking the hTERT (Telomerase Reverse Transcriptase) enhancer, the SV40 enhancer, and the CMV enhancer in this order, are ligated.

The above adenovirus vector containing the DNA construct is obtained by preparing a recombinant adenovirus through introduction of the DNA construct into an adenovirus vector. Introduction of the DNA construct into an adenovirus can be performed by introducing the DNA construct in a pShuttle vector containing the DNA construct of the present invention into an adenovirus, for example.

An adenovirus vector is characterized in that: (1) it enables gene transfer into many types of cells; (2) it enables efficient gene transfer into even cells at the stationary phase; (3) it can be concentrated by centrifugation, and thus a high-titer virus (10-11PFU/ml or more) can be obtained; (4) and it is suitable for direct gene transfer into in vivotissue cells.

As adenoviruses for gene therapy, the first generation adenovirus vector prepared by deleting the E1/E3 region (Miyake, S., et al., Proc. Natl. Acad. Sci. U.S.A., 93, 1320, 1996), the second generation adenovirus vector prepared by deleting, in addition to the E1/E3 region, the E2 or E4 region (Lieber, A., et al., J. Virol., 70, 8944, 1996; Mizuguchi, H. & Kay, M. A., Hum. Gene Ther., 10, 2013, 1999), and the third generation adenovirus vector prepared by almost completely deleting the adenovirus genome (GUTLESS) (Steinwaerder, D. S., et al., J. Virol., 73, 9303, 1999) have been developed. Any of these adenovirus vectors can be used without particular limitation for the gene transfer according to the present invention.

A recombinant adenovirus vector containing the DNA construct that contains REIC/Dkk-3 DNA is administered to a human subject or a subject that is another mammal, so that a gene for cancer therapy is delivered to cancer cells of the subject, the gene is expressed in cancer cells and, tumor cell growth is suppressed so that therapeutic effects are exhibited against cancer.

The adenovirus vector of the present invention can be administered by methods that can be used in the field of gene therapy, such as via intravascular administration (e.g., intravenous administration and intraarterial administration), peroral administration, in-traperitoneal administration, intratracheal administration, intrabronchial administration, subcutaneous administration, or transdermal administration. In particular, the adenovirus vector of the present invention has strong directivity toward a specific tissue or cells, and thus is capable of efficiently delivering a target gene to a specific tissue or cells. Therefore, efficient diagnosis and treatment can be performed even through intravascular administration of the adenovirus vector.

The adenovirus vector may be administered at a therapeutically effective dose, which can be easily determined by persons skilled in the field of gene therapy. Furthermore, the dose can be adequately varied depending on the severity of the pathological condition, gender, age, body weight, lifestyle, and the like of the subject. For example, the adenovirus vector may be administered in doses ranging from $0.5 \times 10^{11}$ to $2.0 \times 10^{12}$ viral genome/kg body weight, preferably ranging from $1.0 \times 10^{11}$ to $1.0 \times 10^{12}$ viral genome/kg body weight, and further preferably ranging from $1.0 \times 10^{11}$ to $5.0 \times 10^{11}$ viral genome/kg body weight. The term "viral genome" represents the number of molecules of the genome of an adenovirus (viral particle count), and is also referred as "particle (s)." That is, the term "viral genome" is the same with the term "viral particles (vp)".

The checkpoint inhibitor such as anti-PD-1 (Programmed cell death 1) antibody and anti-PD-L1 (Programmed cell-death ligand 1) antibody can enhance T-cell responses and mediate antitumor activity. It is well known that various tumor cells including thoracic cancer and malignant mesothelioma are able to upregulate the expression of PD-L, which leads to anergy of cytotoxic T cells upon PD-1 binding to the ligand. Therefore, blocking the PD-1 pathway using anti-PD-1 and anti-PD-L1 antibodies can renovate the immune response against tumor cells. The blocking of the PD-1 pathway is called PD-1 blockade.

The checkpoint inhibitor can be administered in a known way. For example, the dose varies depending on symptoms, age, body weight, and other conditions. A dose of 0.001 mg to 100 mg may be administered at intervals of several days, several weeks, or several months via hypodermic injection, intramuscular injection, or intravenous injection.

The adenovirus vector or the checkpoint inhibitor contains a carrier, a diluent, and an excipient which are generally used in the field of formulation. For example, lactose, magnesium stearate, and the like are used as carriers or excipients for tablets. An aqueous solution is used for injection, such as physiological saline or an isotonic solution containing dextrose or another adjuvant, and this can be used in combination with an appropriate solubilizing agent (e.g., alcohol, polyalcohol such as propylene glycol, and nonionic surfactant). As an oily fluid, sesame oil, soybean oil, or the like is used. As a solubilizing agent, benzyl benzoate, benzyl alcohol, or the like can also be used in combination therewith.

Ad-REIC/Dkk-3 encoded by REIC/Dkk-3 gene can treat or prevent thoracic cancer by upregulating anti-cancer immune system. Further, it induces apoptosis of thoracic cancer cells. Specifically, Ad-REIC/Dkk-3 induces CTLs (cytotoxic T lymphocytes) and the CTLs attack thoracic cancer cells systemically. The thoracic cancer cells attacked by CTLs perform defense function and the thoracic cancer cells express PD-L1. The check point inhibitor inhibits the defense function of the thoracic cancer cells.

Ad-REIC/Dkk-3 alone enhances systemic CD8 T cell priming. Further, Ad-REIC/Dkk-3 alone induces PD-1 on the infiltrating CD8 T cells and presumably PD-L1 in the injected microenvironment. This serves to dampen CD8 (and tumor-specific) T cell expansion. Furthermore, Ad-REIC/Dkk-3 alone leads to higher levels of CD4 memory T cell exhaustion. Combining Ad-REIC/Dkk-3 to anti-PD-1 or anti-PD-L1 enhances a systemic T cell response and anti-tumor responses.

Ad-REIC/Dkk-3 and the checkpoint inhibitor have synergy effect in treating thoracic cancers. Anti-PD-1 and anti-PD-L1 antibodies manipulate the immune system such that cancer expresses PD-1 and PD-L1 on the cell surface making it susceptible to REIC/Dkk-3 gene (REIC/Dkk-3-induced anti-tumor immunity; CTLs induced by REIC/Dkk-3). Combination use of Ad-REIC/Dkk-3 and the checkpoint inhibitor is more effective on the treatment of thoracic cancer than Ad-REIC/Dkk-3 alone or the checkpoint inhibitor alone.

Ad-REIC/Dkk-3 can be administered simultaneously, separately or sequentially with the administration of the checkpoint inhibitor. Ad-REIC/Dkk-3 can also be administered before or after the administration of the checkpoint inhibitor. Preferably, Ad-REIC/Dkk-3 is administered before the administration of the checkpoint inhibitor. When the checkpoint inhibitor is administered separately, the checkpoint inhibitor is administered 1 to 24 hours, 1 to 30 days before or after the administration of Ad-REIC/Dkk-3. Further, the checkpoint inhibitor can be administered at the same interval with Ad-REIC/Dkk-3. The checkpoint inhibitor is administered once when Ad-REIC/Dkk-3 is administered plural times. Alternatively, the Ad-REIC/Dkk-3 is administered once when the checkpoint inhibitor is administered plural times.

Examples of thoracic cancer to be treated herein include, but are not limited to, mesothelioma, especially malignant mesothelioma, lung cancer, chest wall tumors, me-diastinal tumors, pulmonary (lung) nodules, myasthenia gravis tumors, esophageal cancer, thymic cancer or thymoma.

The present invention also comprises a combination, combination preparation or combination pharmaceutical kit comprising Ad-REIC/Dkk-3 and a checkpoint inhibitor.

The present invention also comprises a method for combining Ad-REIC/Dkk-3 with a check point inhibitor in the manufacture of a medicine to treat thoracic cancer.

The present invention also comprises a pharmaceutical composition comprising Ad-REIC/Dkk-3 and a check point inhibitor.

The present invention also comprises a pharmaceutical composition comprising Ad-REIC/Dkk-3 for use in combination with a check point inhibitor.

The present invention also comprises Ad-REIC/Dkk-3 for use in combination with a check point inhibitor.

EXAMPLES

Hereinafter, some embodiments will be described more specifically by way of Examples, but the embodiments not intended to be limited to the following Examples.

Example 1

1. Summary

MTG-201 (Ad5-SGE-REIC/Dkk-3) is a formulation of cancer immunotherapy derived from an adeno vector carrying the REIC/Dkk3 gene. We evaluated anti-cancer activity by local administration of MTG-201 using mouse subcutaneous allograft transplantation model. The model is a syngeneic model with BALB/c strain immunocompetent mouse and AB1 mesothelioma cell line. Two weeks after $5\times10^5$ AB1 cells were inoculated subcutaneously into the shoulder of a mouse, two times of intratumoral administration was performed. The anti-PD-1 antibody and MTG-201 were administered with a single drug or a combination drug, and tumor size measurement was continued until 4 weeks after cell inoculation. As a result, no clear effect on tumor growth was observed in anti-PD-1 antibody alone or MTG-201 alone administration group, but remarkable inhibition of tumor growth was observed in the combination administration group.

2. Method

AB1 cells ($5\times10^5$ in 50 μl of PBS with 500 Matrigel) were injected subcutaneously over the shoulders of 6-week-old BALB/c mice. Two weeks after the injection of AB1 cells, Ad-LacZ, MTG-201 or anti-PD1 antibody in 100 μl of PBS or dilution buffer was injected intratumorally. Based on our preliminary study resulted that tumor could be measured after 2 weeks after AB1 cell injection, adenovirus vectors were injected at days 14 and 16 at a dose of $5.0\times10^{10}$ and anti-PD1 antibody was infected at days 14 and 21. Total injection volume was 1000 each time. Tumor size was measured three times in every week (Mon, Wed, and Fri) for 4 weeks after AB1 cell injection, and mice were sacrificed on day 28. Tumors were excised and tumor weight was measured.

The protocol at a glance was shown in FIG. 3.

Or we will start to inject the viral vector into mice when mean tumor volume is over 5 mm$^3$ or 10 mm$^3$. Preliminary study showed that we could detect mass lesion 2 weeks after injection and mean tumor volume at that time was 13.15 mm$^3$.

3. Results

Figure 4:
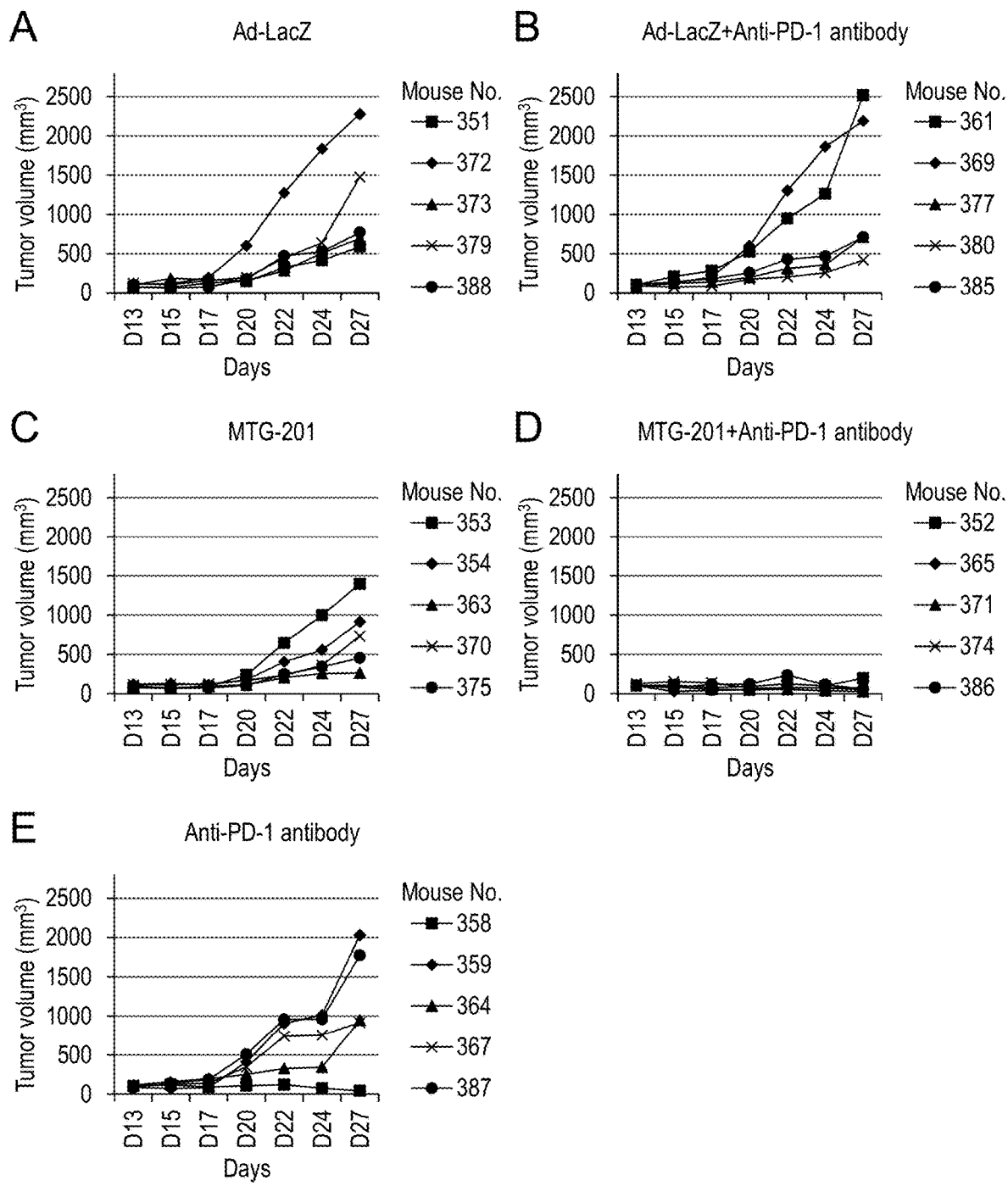
FIG. 4A-4E shows tumor volume change for each mouse in MTG-201 SC model.
Figure 5:
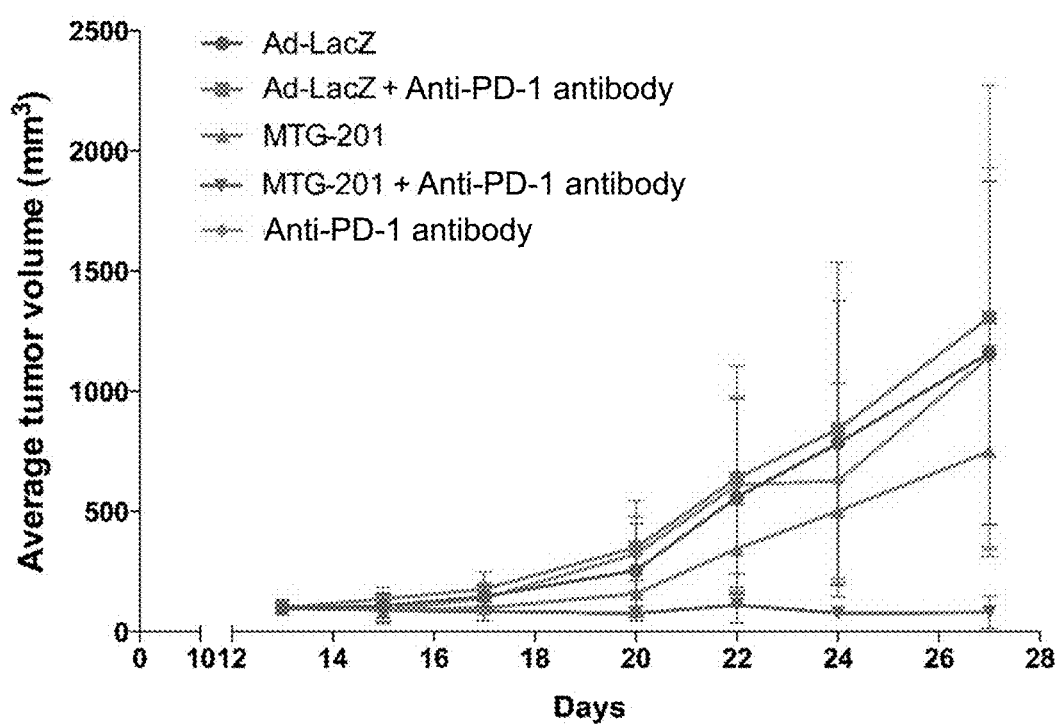
FIG. 5 shows average tumor volume change for five mice in MTG-201 SC model.
Figure 6:
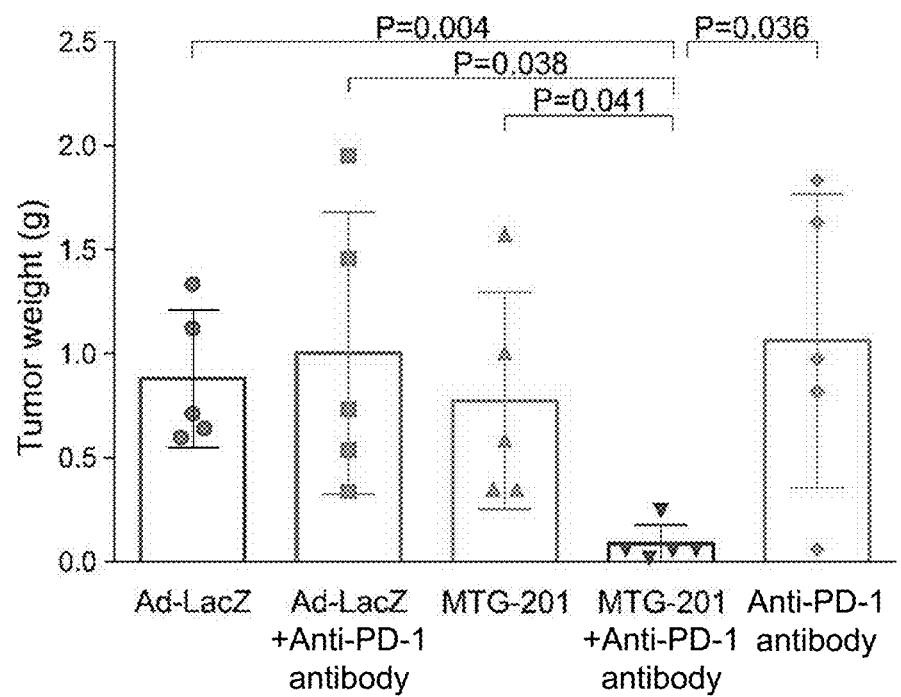
FIG. 6 shows dissected tumor weight of five mice in MTG-201 SC model.

FIG. 4 shows the tumor volume changes each mouse of the five mice. FIG. 4A, FIG. 4B, FIG. 4C, FIG. 4D and FIG. 4E show the tumor volume changes of mice administered with Ad-LacZ alone, Ad-LacZ+anti-PD1 antibody, MTG-201 alone, MTG-201+anti-PD1 antibody and anti-PD-1, respectively. FIG. 5 shows the average tumor volume changes. FIG. 6 shows average tumor weight of the five mice. As demonstrated by FIGS. 4, 5 and 6, the administration of MTG-201 in combination with anti-PD1 antibody suppressed the growth of cancer.

Example 2: Adenoviral-Mediated DKK3 Gene Transfer for Overcoming Resistance to PD-1 Blockade in Malignant Mesothelioma Objectives: Immunotherapy with PD-1 blockade is a promising therapeutic strategy for the treatment of malignant mesothelioma (MM), however objective response rates from early phase trials are only approximately 20%. We hypothesized that resistance of MM to PD-1 inhibition can be overcome by stimulating intratumoral lymphocyte infiltration through local gene transfer of the DKK3 gene which encodes the Reduced Expression in Immortalized Cell (REIC) protein, a pro-apoptotic protein and tumor-suppressor, using a replication incompetent adenoviral vector (Ad-REIC).

Methods: REIC protein expression was evaluated after in vitro treatment of AB1 mouse MM cells using time-of-flight mass cytometry (CyTOF). In a well-established immunocompetent model of mouse MM, $5 \times 10^5$ AB1 mouse MM cells were subcutaneously injected into syngeneic BALB/c mice on day 0. Ad-REIC ($5 \times 10^{10}$ viral particles) was administered intratumorally on days 13 and 15, and anti-mouse PD-1 antibody (250n) was administered intratumorally on days 13 and 20. CyTOF was used to evaluate the tumor immune microenvironment of treated tumors on day 27.

Figure 7:
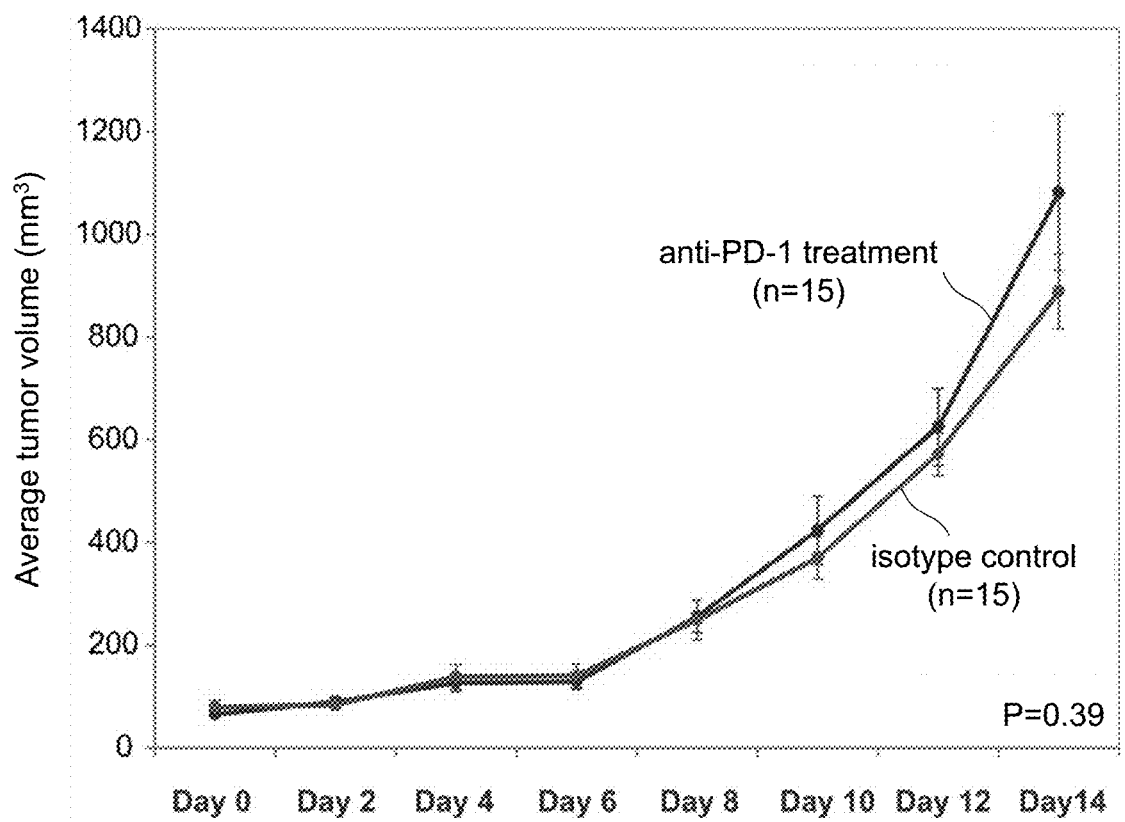
FIG. 7 shows resistance of established AB1 MM tumors to PD-1 blockade.
Figure 8:
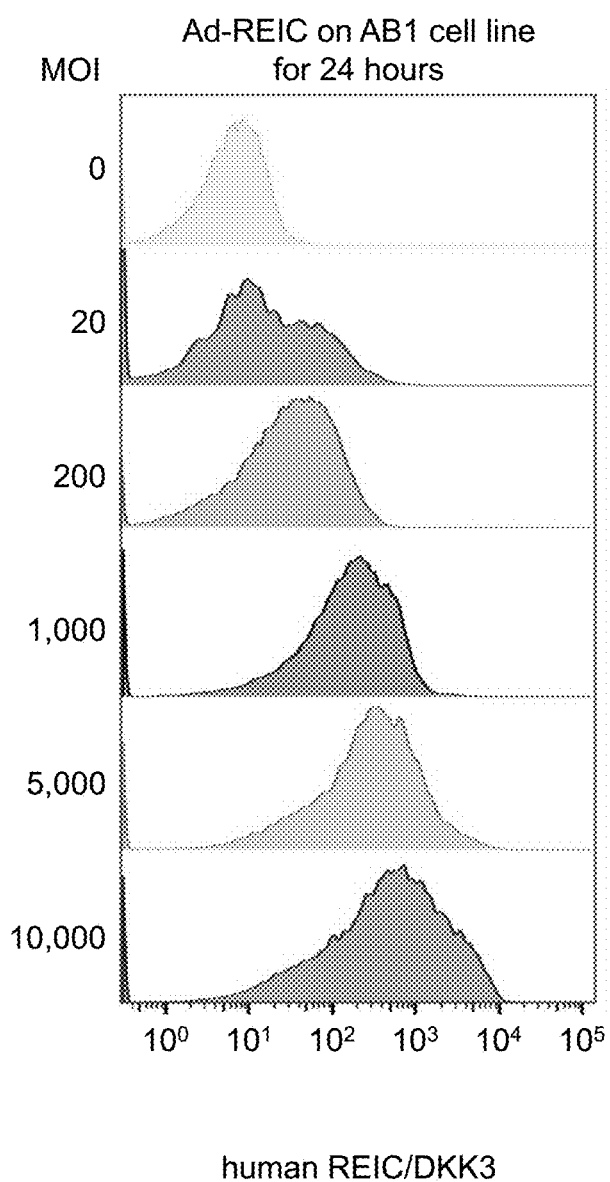
FIG. 8 shows a dose-dependent increase of REIC protein expression in mouse AB1 cells.
Figure 9:
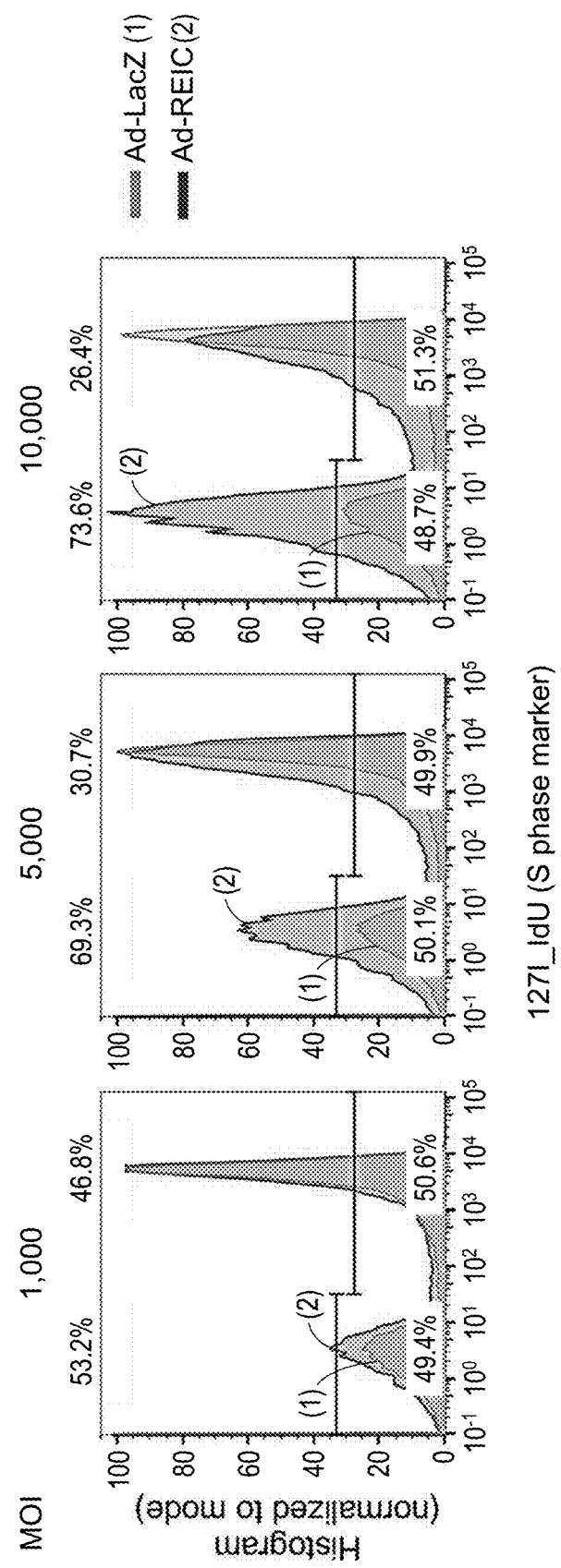
FIG. 9 shows S phase arrest of the cell cycle by REIC protein expression.
Figure 10:
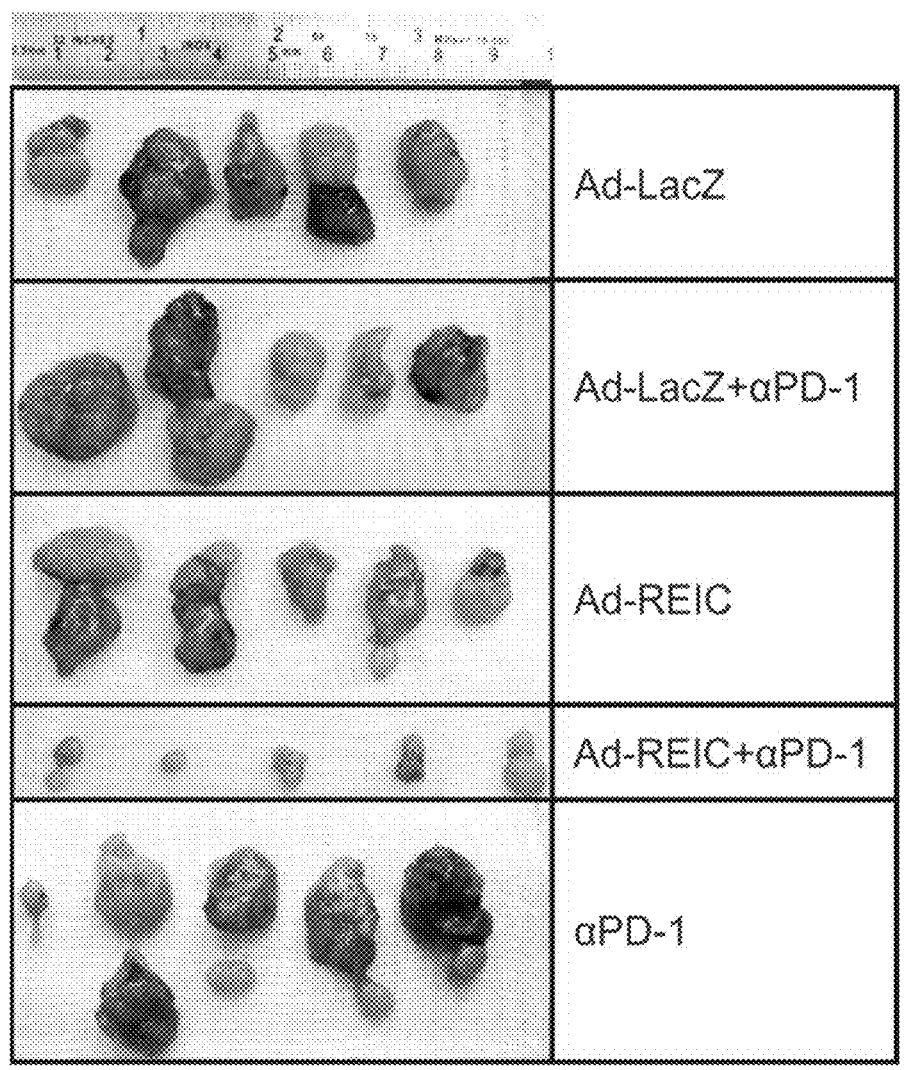
FIG. 10 shows suppression of tumor growth by combination therapy of Ad-REIC and anti-PD-1 antibody (photograph).
Figure 11:
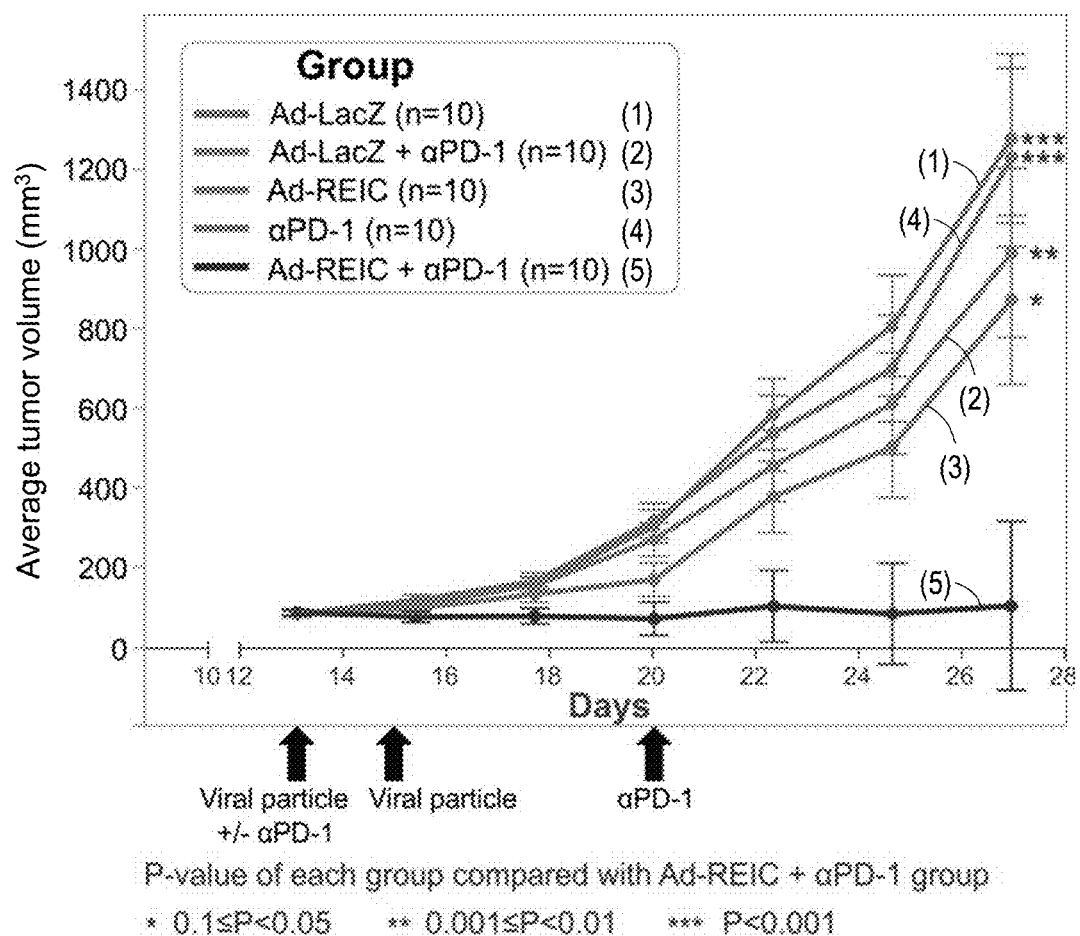
FIG. 11 shows suppression of tumor growth by combination therapy of Ad-REIC and anti-PD-1 antibody (graph).
Figure 12:
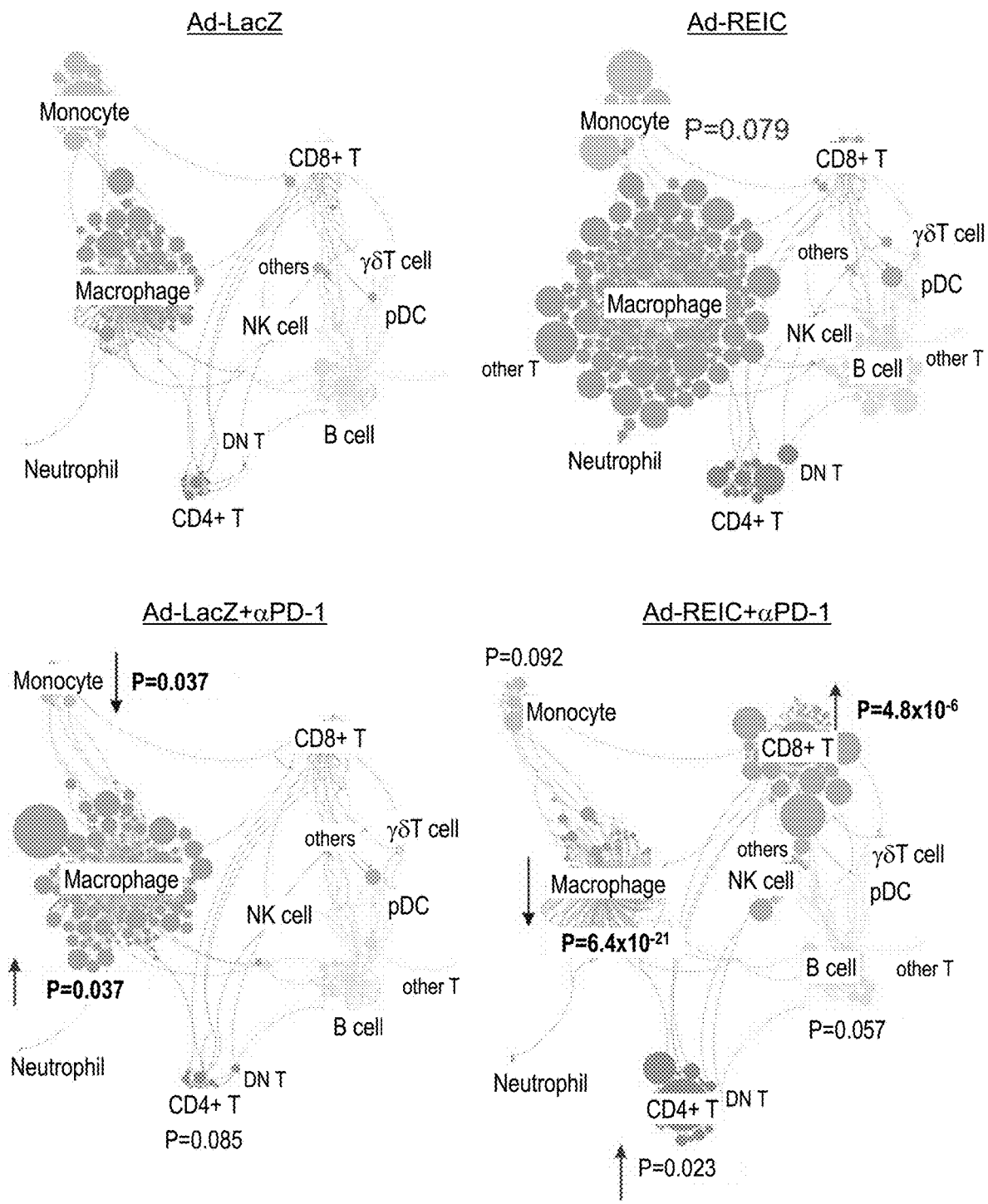
FIG. 12 shows increase of CD8 T cells and decrease of tumor associated macrophages by Ad-REIC plus anti-PD-1 antibody.
Figure 13:
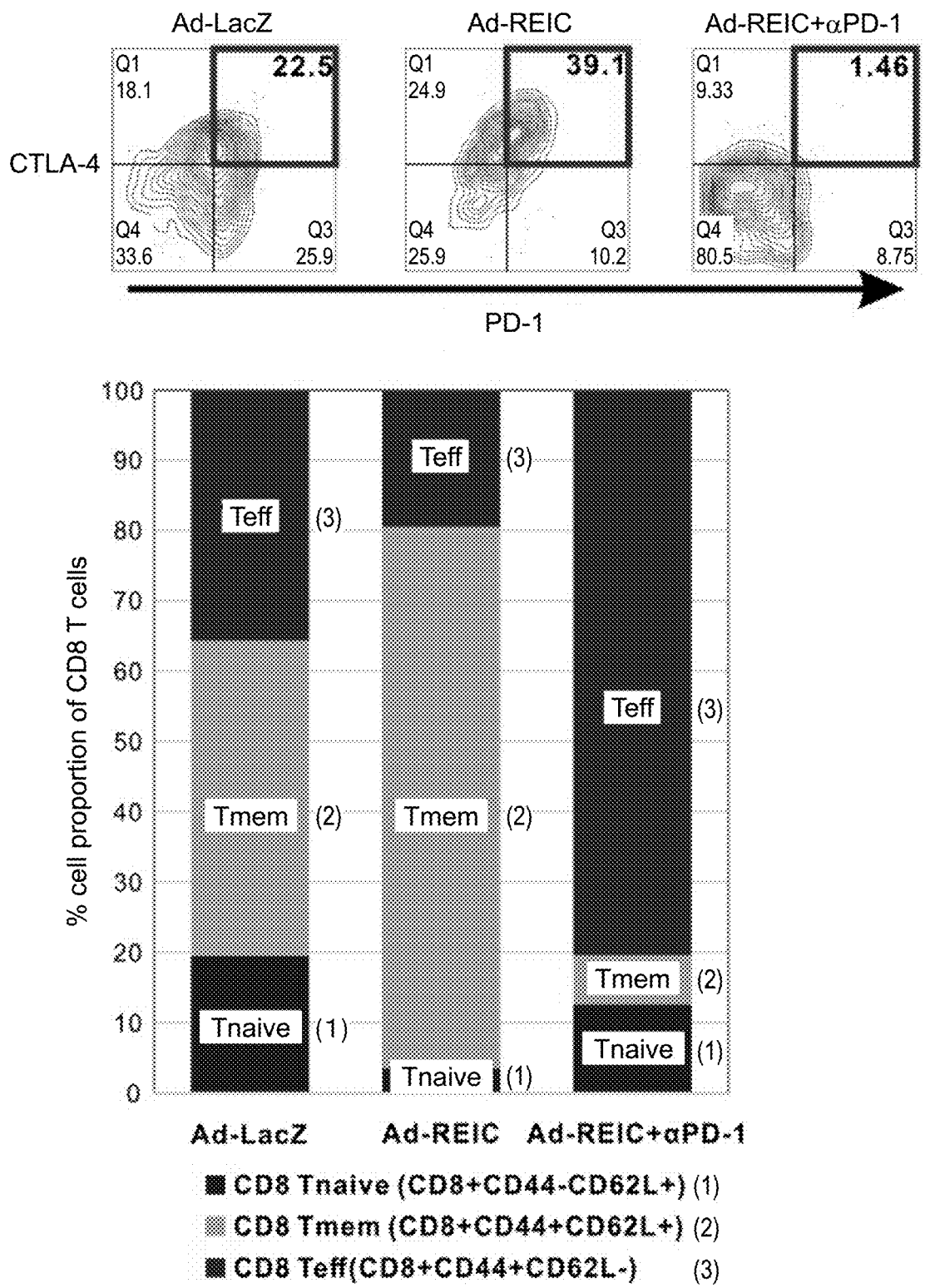
FIG. 13 shows reinvigoration of CD8 T cells by PD-1 blockade.

Results: Established AB1 MM tumors were resistant to PD-1 blockade (FIG. 7). REIC protein expression in mouse AB1 cells increased in a dose-dependent manner following treatment with Ad-REIC in vitro (FIG. 8) and resulted in S phase arrest of the cell cycle (FIG. 9). Treatment of mice bearing AB1 MM tumors with combination Ad-REIC and anti-PD-1 antibody strikingly suppressed tumor growth (FIGS. 10 and 11). CyTOF performed on single cell suspensions from treated AB1 tumors demonstrated that Ad-REIC plus anti-PD-1 antibody resulted in increased numbers of CD8 T cells and decreased numbers of tumor-associated macrophages (CD45+F4/80+CD64+CD3-CD19-) (FIG. 12). Following Ad-REIC therapy, the proportion of partially exhausted CD8 T cells (CD8+PD1+CTLA-4) increased from 22% to 39%, and combination therapy resulted in decreased frequencies of partially exhausted CD8 T cells (1.5%) and increased frequencies of effector CD8 T cells (CD8+CD44+CD62L-), implying reinvigoration of CD8 T cells by PD-1 blockade (FIG. 13).

Figure 14:
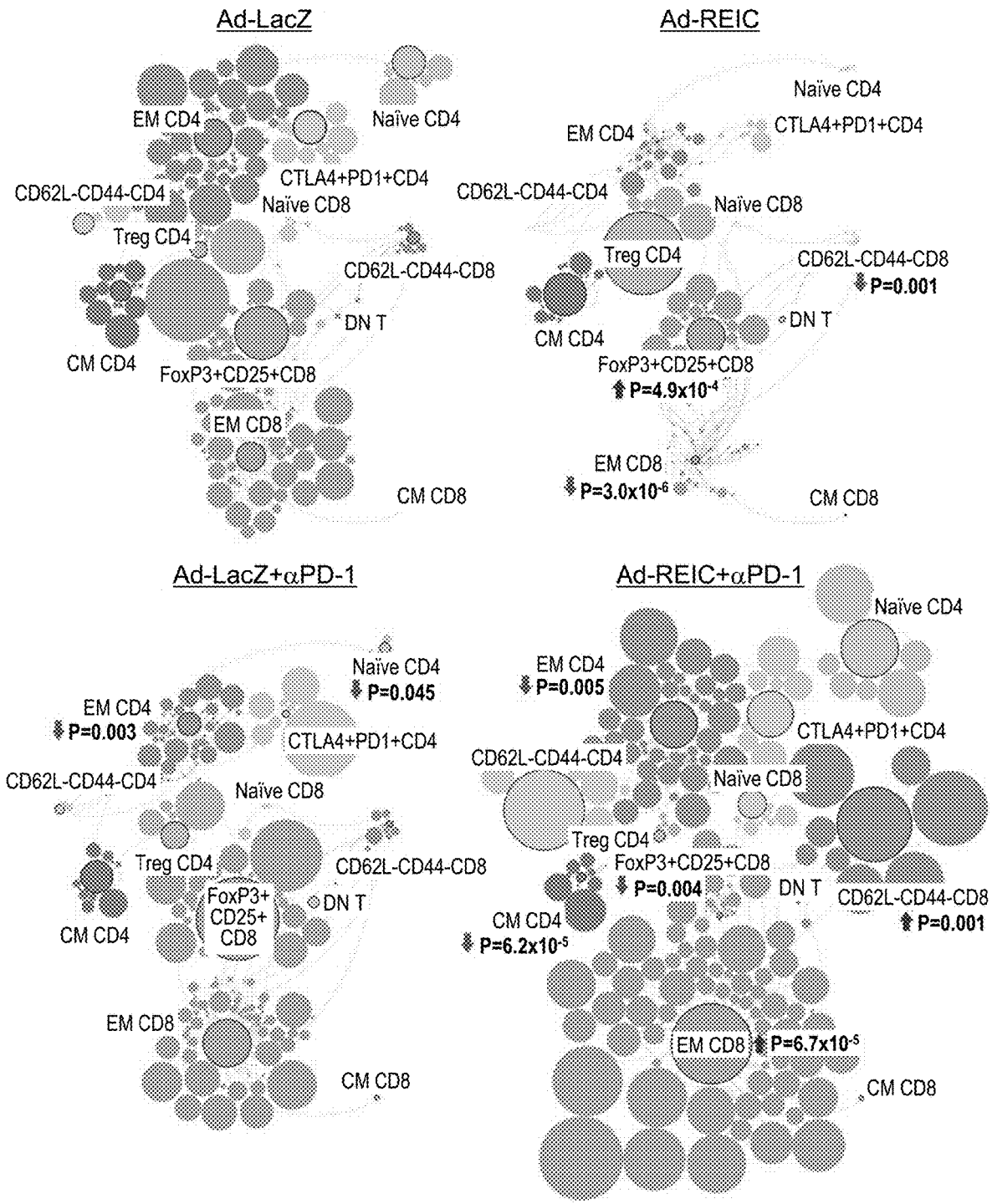
FIG. 14 shows increase of effector memory CD8 T cells and decrease of Treg cells (regulatory T cells) by Ad-REIC plus anti-PD-1 antibody.

Deeper characterization of T cell population revealed abundant recruitment of effector memory CD8 (EM CD8) T cells after Ad-REIC and anti-PD-1 combination therapy. Further, effector CD8 T cells (CD62L-CD44-CD8) and naive CD4 T cells increased and Treg cells (regulatory T cells) decreased (FIG. 14).

Conclusions: Our results demonstrate that resistance to anti-PD-1 antibody immunotherapy in mouse MM can be overcome by adenovirus-mediated REIC gene transfer. This strategy has promising potential as a novel immunotherapeutic approach for patients with mesothelioma and will be tested in a phase II clinical trial at our in-stitution.

Example 3: Effect of Combined Use of Ad-SGE-REIC and Anti-PD-1 Antibody in EGFR Mutant Lung Cancer Model Methods: Tumor cells subcultured in vivo are transplanted subcutaneously into the dorsal region of C57BL/6J mice, and 7 days after transplantation Ad preparation (Ad-LacZ, Ad-SGE-REIC) $1.0 \times 10^9$ ifu was administered intratumorally at days 1 and 3 and 200 µg of anti-PD-1 antibody was administered intraperitoneally at day 1. The tumor volume of each group was measured over time.

Figure 15:
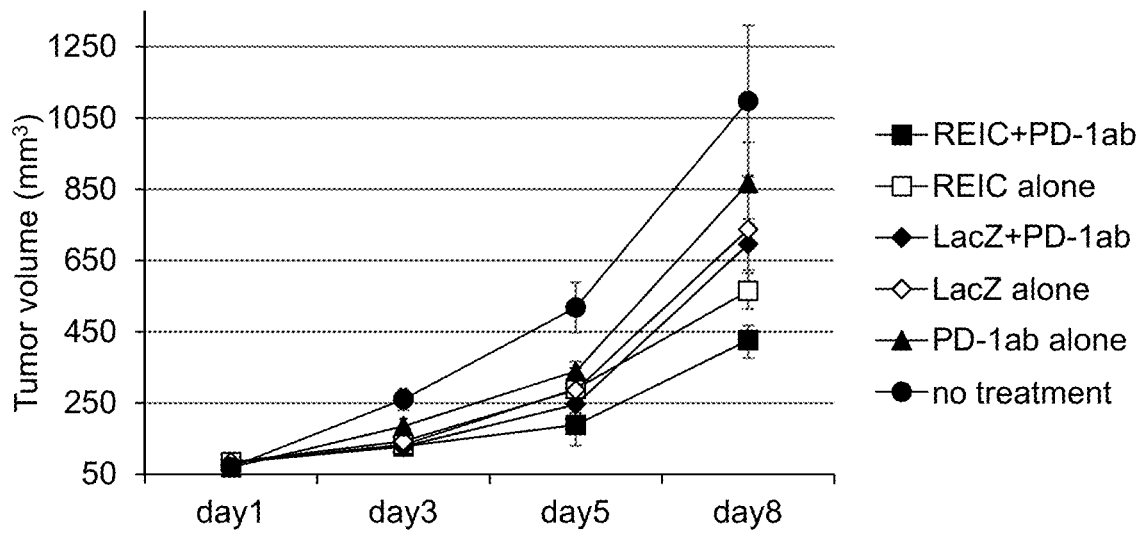
FIG. 15 shows antitumor effect of the combined use of the Ad-SGE-REIC preparation and anti-PD-1 antibody.

Results: The results are shown in FIG. 15. The combined use of the Ad-SGE-REIC preparation and anti-PD-1 antibody showed a clearly stronger antitumor effect compared to the Ad preparation alone or the combined use of the Ad negative control preparation (Ad-LacZ) and the anti-PD-1 antibody.

All publications, patents, and patent applications cited herein are incorporated herein by reference in their entirety.

The invention claimed is:

1. A method for treating thoracic cancer which is resistant to anti-PD-1 or anti-PD-L1 antibody immunotherapy, comprising administering to a subject with thoracic cancer a combination consisting of an Ad-REIC/Dkk-3, a check point inhibitor, and a carrier, wherein the Ad-REIC/Dkk-3 is an adenovirus vector comprising:
   (i) a CMV promoter;
   (ii) the following REIC/Dkk-3 DNA:
      (a) DNA comprising the nucleotide sequence shown in SEQ ID NO: 1, or
      (b) DNA having at least 90% sequence identity with the nucleotide sequence shown in SEQ ID NO:1,
   (iii) a polyA sequence; and
   (iv) enhancers prepared by linking an human Telomerase Reverse Transcriptase (hTERT) enhancer, an SV40 enhancer, and a CMV enhancer, wherein the hTERT enhancer is 5' of the SV40 enhancer, and the SV40 enhancer is 5' of the CMV enhancer,
   wherein the thoracic cancer is a mesothelioma or an EGFR-mutant lung cancer.

2. The method of claim 1, wherein the check point inhibitor is an anti-PD-1 antibody or an anti-PD-L1 antibody.

3. The method of claim 1, wherein the check point inhibitor is an anti-PD-1 antibody.

4. The method of claim 1, wherein the check point inhibitor is an anti-PD-L1 antibody.

5. The method of claim 1, wherein the thoracic cancer is a mesothelioma.

6. The method of claim 1, wherein the thoracic cancer is EGFR-mutant lung cancer.

* * * * *